United States Patent [19]

Tanaka et al.

[11] 4,278,101
[45] Jul. 14, 1981

[54] APPARATUS FOR CLEANING ENDOSCOPE

[75] Inventors: Masahiro Tanaka, Tokyo; Katunaga Konoshima, Hachioji, both of Japan

[73] Assignee: Olympus Optical Co., Ltd., Japan

[21] Appl. No.: 70,620

[22] Filed: Aug. 29, 1979

[30] Foreign Application Priority Data

Nov. 27, 1978 [JP] Japan .............................. 53-146300

[51] Int. Cl.³ .............................................. B08B 3/02
[52] U.S. Cl. ................................ 134/167 C; 134/171;
134/181; 134/199; 239/248
[58] Field of Search ................................... 134/99–102,
134/137, 153, 165, 167 C–168 C, 171, 180–181,
198–200; 239/246, 248

[56] References Cited

U.S. PATENT DOCUMENTS

| 3,092,120 | 6/1963 | Hilger et al. | 134/100 X |
| 3,104,407 | 9/1963 | Volk | 134/181 X |
| 3,648,931 | 3/1972 | Jacobs | 239/248 |
| 4,064,886 | 12/1977 | Heckele | 134/171 X |

FOREIGN PATENT DOCUMENTS

| 51-25493 | 2/1976 | Japan | 134/199 |
| 51-140590 | 11/1976 | Japan | 134/199 |
| 52-87066 | 6/1977 | Japan | 134/199 |
| 105589 | 9/1942 | Sweden | 134/200 |

Primary Examiner—Robert L. Bleutge
Attorney, Agent, or Firm—Ostrolenk, Faber, Gerb & Soffen

[57] ABSTRACT

An apparatus for cleaning an endoscope comprises an upper spray head which is disposed toward the central axis of a rinse vessel, and a lower spray head disposed toward the wall of the rinse vessel. A portion of an endoscope is disposed around the central axis of the rinse vessel, and the spray heads direct a cleaning liquid toward the endoscope portion from above and below in an oblique direction while rotating about the central axis. The spray heads do not have to be removed to place or remove an endoscope portion to be cleaned.

8 Claims, 4 Drawing Figures

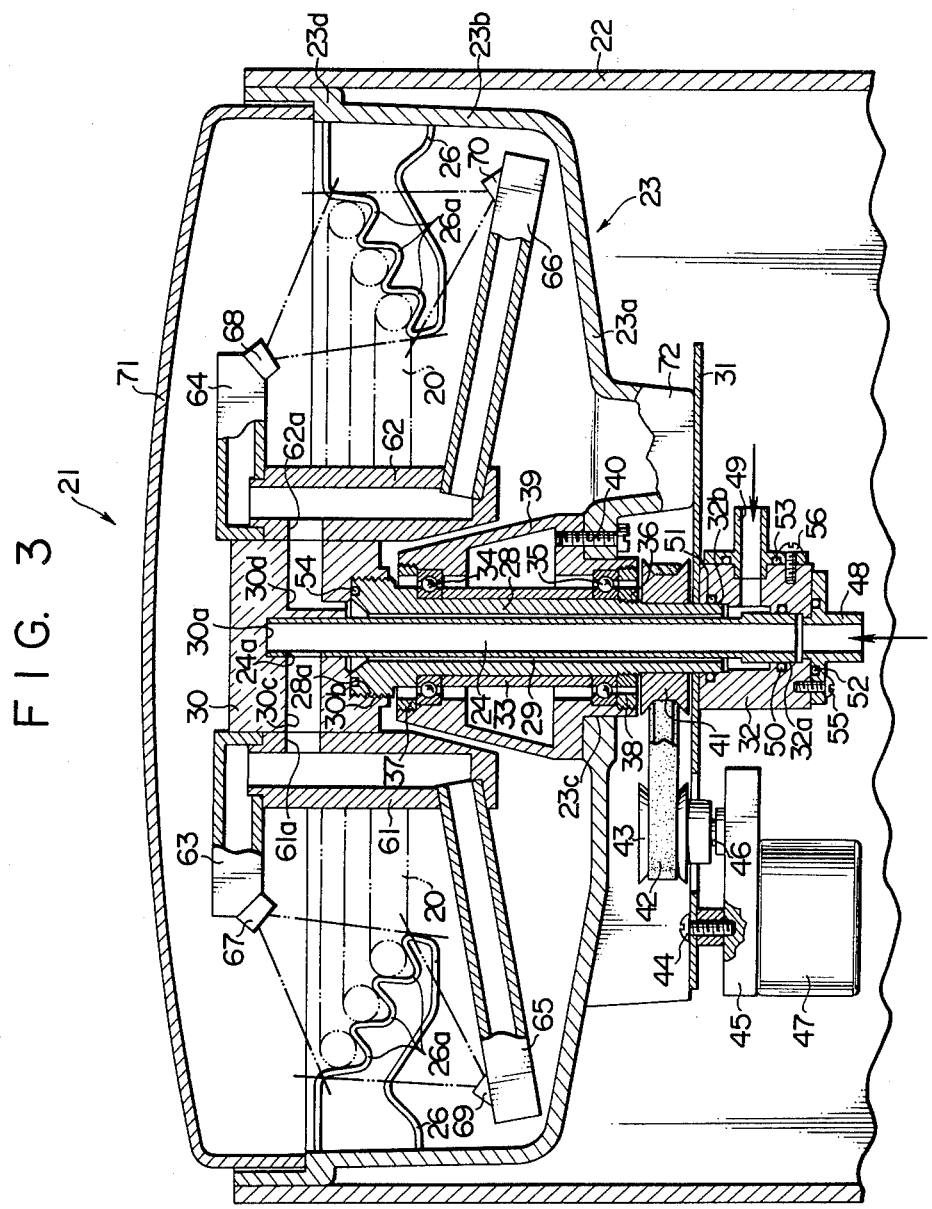

APPARATUS FOR CLEANING ENDOSCOPE

BACKGROUND OF THE INVENTION

The invention relates to an apparatus for cleaning an endoscope, and more particularly, to an apparatus for cleaning a distal end of an endoscope which is inserted into coeloma and used therein.

As is well recognized, an endoscope which is used for the medical purpose of obtaining an observation of an affected area within coeloma comprises an elongate flexible tube internally containing an observation and an illumination optical system, each formed of a bundle of optical fibers and which is adapted to be inserted into coeloma, and an operating end which remains outside the coeloma to permit various manual operations. When the distal end of the endoscope is withdrawn from the coeloma after the termination of diagnosis or therapy with the endoscope, it has coeliac fluid, blood and other contaminants on it. Hence, it is necessary to clean and sterilize the distal end of the endoscope which has been inserted into the coeloma in order to permit its repeated use.

By way of Example, FIGS. 1 and 2 show a side elevation partly in section and a plan view, respectively, of a conventional cleaning apparatus which is used to clean the distal end of a used endoscope. Referring to these Figures, cleaning apparatus 1 comprises cylindrical frame 2, to the top of which is secured rinse vessel 3 in the form of a hollow cylinder having bottom plate 3a. Hollow drive shaft 4 extends through bottom plate 3a in alignment with the axis of vessel 3, and a pair of spray heads 8a, 8b have one end joined together and are secured thereat to the top of drive shaft 4 and have their free end extending toward cylindrical wall 3b of rinse vessel 3 at an upper and a lower level, respectively. A plurality of circumferentially spaced and radially extending support members 6 have one end fixed to the inner surface of cylindrical wall 3b of rinse vessel 3 and have another end extending radially inward in a plane which is located intermediate spray heads 8a, 8b. Drive shaft 4 is adapted to be driven for rotation by a motor, not shown, and internally houses liquid feed pipe 5 through which a cleaning liquid such as water, a detergent solution or a sterilizing solution is supplied to spray heads 8a, 8b.

A plurality of circular spray apertures 9a, 9b are formed in spray plates 10a, 10b which are fitted into the bottom of upper spray head 8a and into the top of lower spray head 8b, respectively. The radially inner end of upper spray head 8a is formed into a cylindrical shape so as to be pivotally mounted on base 7. When a portion of the endoscope, indicated in phantom by numeral 20, which has been inserted into the coeloma is to be mounted on support members 6, upper spray head can be moved to position 8aA shown in phantom in FIG. 2. Support members 6 comprise metal wires having a plurality of radially spaced depressions 6a formed therein, and the portion 20 of the endoscope which is to be cleaned is spirally coiled to be received in these depressions 6a. In this manner, depressions 6a serve to locate the portion 20 of the distal end in a cleaning position. A liquid drain shown by numeral 11 is formed in bottom plate 3a of rinse vessel 3.

In operation, the portion 20 of the endoscope is placed on and supported by depressions 6a of support members 6. Subsequently, cleaning water is supplied to spray heads 8a, 8b through feed pipe 5, and thence directed to the upper and lower surfaces of the portion 20 through spray apertures 9a, 9b, thus cleaning the outer surface of endoscope portion 20. At the same time, drive shaft 4 is driven for rotation to cause heads 8a, 8b to rotate about the axis of shaft 4. One revolution of heads 8a, 8b is effective to rinse the portion 20 with water over its entire length. When the water rinsing operation is completed, a sterilizing solution is fed to spray heads 8a, 8b through feed pipe 5, sterilizing the portion 20 in the same manner as in the water rinse operation.

When apparatus 1 is used, the upper spray head 8a interferes with the placement in and removal from apparatus 1 of the portion 20 of the endoscope. Hence, head 8a is moved to position 8aA shown in phantom line in FIG. 2, and after the portion 20 is placed on depressions 6a of support members 6, the upper head 8a is returned to its original position. It will be seen that such operation and the required construction therefor are undesirable. In addition, there is an apparatus known which is provided with a plurality of pairs of spray heads 8a, 8b in order to increase the cleaning efficiency. It is apparent that the placement and removal of the portion 20 of the endoscope is still more troublesome with such an apparatus.

Spray plates 10a, 10b of spray heads 8a, 8b are formed with a multiplicity of circular spray apertures 9a, 9b, and it is customary that the diameter of these apertures 9a, 9b be reduced in order to increase the injection speed of the cleaning liquid, and to provide an increased spacing between these apertures. This results in the problem that apertures 9a, 9b are liable to be plugged, and the increased spacing between these apertures disadvantageously causes non-uniform cleaning of the endoscope portion 20.

When the sterilization process follows the water rinse operation, any residue of cleaning water which remains within feed pipe 5 and spray heads 8a, 8b may dilute the sterilizing liquid, either preventing an effective sterilization effect or requiring an increased amount of sterilizing solution.

SUMMARY OF THE INVENTION

It is an object of the invention to provide an apparatus for cleaning an endoscope which eliminates the above disadvantages.

In accordance with the invention, an upper spray head or heads are disposed toward the central axis of a rinse vessel, and are not located above a cleaning station or position, thus avoiding interference by them or by a central hollow drive shaft with the placement or removal of a distal end or an inner end of the endoscope on the cleaning position in spiral form. This eliminates the need to move the spray head or heads when placing or removing the endoscope. Because the spray apertures are in the form of slits, their plugging is prevented, assuring a uniform cleaning operation. Additionally, a plurality of pairs of upper and lower spray heads are provided. At least one pair of these heads is connected with a liquid feed path which is independent from that of the remaining pairs, so that sterilizing solution and water can be supplied by separate paths, so that the sterilizing solution will not be diluted with any residue of cleaning water which remains in the feed tube.

BRIEF DESCRIPTION OF THE DRAWINGS

FIG. 3 is a cross section of an apparatus for cleaning an endoscope which is constructed in accordance with one embodiment of the invention.

DESCRIPTION OF PREFERRED EMBODIMENT

Figure 1:
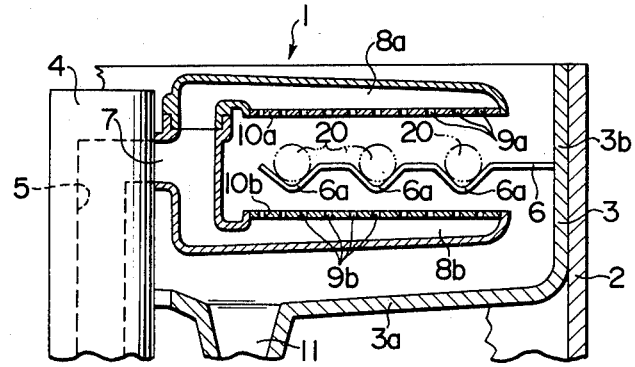
FIG. 1 is a side elevation, partly in section, of a conventional apparatus for cleaning an endoscope.
Figure 2:
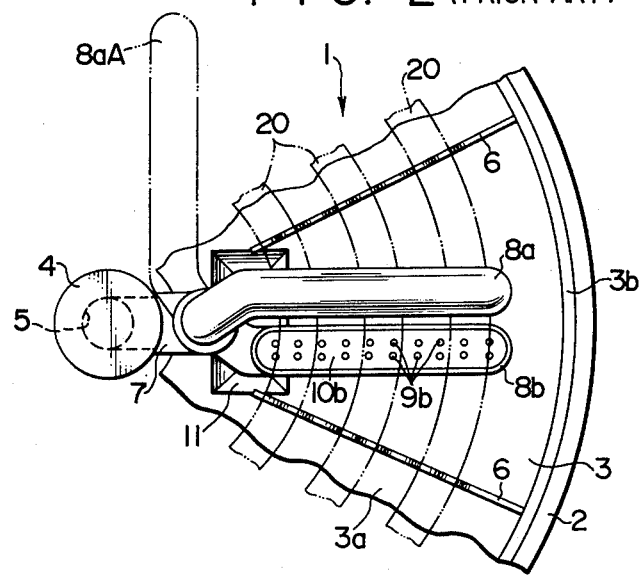
FIG. 2 is a plan view of the apparatus shown in FIG. 1.

Referring to FIG. 3, there is shown an apparatus 21 for cleaning an endoscope which is constructed according to the invention. Apparatus 21 essentially comprises cylindrical rinse vessel 23 having bottomplate 23a and which is fitted into and secured to the upper end of cylindrical frame 22, which defines the outer wall of the apparatus. Bottomplate 23a is centrally formed with opening 23c through which extends liquid feed hollow shaft 24, which is rotatable relative to rinse vessel 23. Hollow drive shaft 28 is rotatably disposed around hollow shaft 24 and defines gap 29 therewith. Gap 29 also serves the function of supplying a liquid. Liquid feed path forming member 30 is secured to the top end of shaft 24 and defines a plurality of liquid feed paths which are connected with liquid feed tubes 63 to 66 secured thereto. A plurality of spray heads 67 to 70 are mounted on the free end of liquid feed tubes 63 to 66. A plurality of support members 26 have both ends secured to inner cylindrical wall 23b of rinse vessel 23 and extend toward the center of vessel 23, these support members 26 being adapted to carry a distal end or an inner end of an endoscope thereon.

Liquid feed shaft 24 is loosely inserted into hollow shaft 28 to form gap 29 therebetween, and has its upper end fitted into cylindrical hole 30a formed in square pillar-shaped member 30. The lower end of shaft 24 is rotatably fitted into central bore 32a of coupler mount 32, which is integrally secured to the underside of support plate 31, which is in turn fixedly mounted on a stationary member of apparatus 21. The upper end of hollow shaft 28 is peripherally formed with threads 28a, which are engaged by threads 30b formed on member 30, with O-ring 54 interposed between the upper end of hollow shaft 28 and member 30. The lower end of hollow shaft 28 is rotatably fitted into central bore 32b formed in coupler mount 32, with O-ring 51 interposed therebetween.

Intermediate its length, hollow shaft 28 is peripherally provided with cylindrical distance piece 33, the upper and lower ends of which fixedly carry the inner races of bearings 34, 35, the outer races of which are secured to bearing frame 39 by means of nuts 36, 37, 38, whereby hollow shaft 28 is rotatably supported by frame 39. Frame 39 is in the form of a truncated cone through which shafts 24 and 28 extend, and has its lower end secured within central bore 23c formed in rinse vessel 23 by means of set screw 40. In a region projecting downwardly through frame 39, drive shaft 28 fixedly carries drive pulley 41, which is coupled through belt 42 with output pulley 43, which is in turn fixedly mounted on drive shaft 46 extending upwardly from gear box 45, secured to support plate 31 by means of set screw 44. Drive shaft 46 is connected with the output shaft of drive motor 47 through a reduction gearing located within gear box 45.

Feedwater fitting 48 is disposed on the underside of coupler mount 32 and secured thereto by set screw 55 with O-ring 52 interposed therebetween, fitting 48 communicating with the interior of liquid feed shaft 24. Similarly, fitting 49 which is adapted to supply a sterilizing solution is disposed in abutment against a side of coupler mount 32 and communicates with gap 29 formed between shafts 24, 28. Fitting 49 is secured to mount 32 by set screw 56, with an O-ring 53 interposed therebetween. In this manner, the interior of shaft 24 represents a feedwater path while gap 29 defined between the shafts 24, 28, represents a supply path for another liquid. It will be appreciated that O-rings 50 to 54 are effective in preventing the leakage and the mixture of cleaning water and a sterilizing solution feed in via gap 29. Adjacent to its upper end, liquid feed shaft 24 has opening 24a formed in its sidewall, which communicates with feedwater path 30c formed in member 30. Member 30 is also formed with liquid feed path 30d which communicates with gap 29 defined between shafts 24, 28. It will be noted that these paths 30c, 30d communicate with openings 61a, 62a, respectively, which are formed in the sidewall of liquid supply tube mounting members 61, 62, which are in turn fixedly mounted on the sidewall of member 30.

Figure 4:
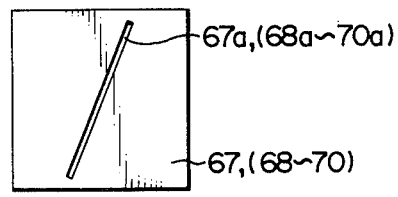
FIG. 4 is a plan view showing the configuration of a spray aperture formed in a spray head which is used in the apparatus shown in FIG. 3.

Mounting members 61, 62 comprise elongate pipes which have their upper end connected with horizontally and radially extending liquid feed tubes 63, 64, respectively, each having a relatively small length. The lower ends of mounting members 61, 62 are connected with liquid feed tubes 65, 66 having a relatively great length and which extend both radially and slightly downward. Upper spray heads 67, 68 are mounted on the free end of liquid feed tubes 63, 64 in a downward and outward orientation while lower spray heads 69, 70 are mounted on the free end of liquid feed tubes 65, 66 in an upward and inward orientation. Upper spray head 67 and lower spray head 69 are spaced apart and face-to-face as are upper spray head 68 and lower spray head 70. Slit-shaped spray apertures 67a to 70a (see FIG. 4), which have a given angle of inclination with respect to the axis of the spray head, are formed in that surface of each spray head 67 to 70 which opposes the corresponding spray head with which it is face-to-face.

Support members 26 mentioned above extend into positions intermediate the oppositely located spray heads 67 and 69 or 68 and 70 in order to receive the distal end or inner portion 20 (shown in phantom) of an endoscope which has been inserted into the coeloma, at a cleaning position. These support members 26 are formed of metal wires which are folded to define a plurality of depressions 26a in which the successive turns of endoscope portion 20 are received. The opposite ends of support members 26 are secured to cylindrical wall 23b of rinse vessel 23. It will be appreciated that the endoscope portion 20 is spirally disposed on depressions 26a of support members 26.

In FIG. 3, numeral 71 represents a top cover of apparatus 21 while numeral 72 represents a liquid drain disposed in bottomplate 23a of rinse vessel 23. It will be seen that the edge of top cover 71 bears against step 23d formed on cylindrical wall 23b of rinse vessel 23.

In operation, portion 20 of the endoscope which has been inserted into the coeloma is disposed in a spiral form on depressions 26a of support member 26. Then a feed pump, not shown, is operated to supply cleaning water through fitting 48. The cleaning water is fed through liquid supply shaft 24, feed water path 30c, the interior of mounting member 61 and liquid feed tubes 63, 65 to spray heads 67, 69. The cleaning water supplied to upper spray head 67 is sprayed through spray aperture 67a formed therein and directed downwardly and outwardly as indicated by phantom line, spreading lengthwise of the slit. Similarly, the cleaning water supplied to lower spray head 69 is directed through aperture 69a upward and inwardly while spreading lengthwise of the slit. The spray of this cleaning water impinges on the endoscope portion 20 disposed on support members 26, thus cleaning its outer surface.

At the same time, motor 47 is set in motion, whereby the rotation of motor 47 is transmitted through output pulley 43 and drive pulley 41 to hollow drive shaft 28. Since hollow shaft 28 is integral with member 30, mounting members 61, 62 and liquid feed tubes 63 to 66, spray heads 67, 69 undergo a rotation while spraying the cleaning water, whereby the entire length of the endoscope portion 20 is cleaned. The full length of the endoscope portion 20 is completely cleaned during one revolution of hollow drive shaft 28. To enable the endoscope portion 20 to be sterilized, a liquid feed pump, not shown, is energized together with motor 47 to supply a sterilizing solution into fitting 49. The sterilizing solution is fed through gap 29 defined between shafts 28, 24, liquid feed path 30d, the interior of mounting member 62, liquid feed tubes 64, 66 to spray heads 68, 70. The sterilizing solution supplied to spray heads 68, 70 is sprayed through apertures 68a, 70a in the same manner as the cleaning water, thus rinsing the outer surface of the endoscope portion 20 with the sterilizing solution. Simultaneously, motor 47 is energized to drive hollow shaft 28 for rotation, whereby the entire length of the endoscope portion 20 can be sterilized as before.

In the embodiment described above, a pair of spray heads 67, 69 are used to direct the cleaning water and a pair of spray heads 68, 70 are used to direct the sterilizing solution, but it will be readily understood that any number of such spray heads may be used as desired.

What is claimed is:

1. An apparatus for cleaning an endoscope, said apparatus comprising:
    a rinse vessel adapted to receive a portion of an endoscope to be cleaned, said rinse vessel having a center and an outer wall;
    support means in said rinse vessel defining a conical support plane around said center of said rinse vessel, said support means being for supporting one or more endoscope portions in said conical support plane;
    first and second spray heads; said first spray head being disposed in said rinse vessel relatively near said center of said rinse vessel as compared with said second spray head and second spray head being disposed in said rinse vessel relatively near said outer wall as compared with said first spray head; said first spray head including means for spraying the endoscope portion in a first direction generally perpendicular to said conical support plane when the endoscope portion is supported in said support plane, and said second spray head including means for spraying the endoscope portion in a second direction generally perpendicular to said conical support plane when the endoscope portion is supported in said support plane, said first and second directions being directly opposite to each other;
    means for feeding liquid to said spray heads; and
    drive means for rotating said spray heads about said center of said rinse vessel and said spray heads rotating in respective parallel planes with respect to which said support plane is inclined.

2. An apparatus according to claim 1, wherein each of said nozzles is a slit-shaped spray aperture.

3. An apparatus according to claim 1, further including:
    a hollow drive shaft rotatably disposed at said center of said rinse vessel, the hollow interior of said drive shaft defining a liquid feed path;
    a feed path forming member secured to said drive shaft;
    a mounting member fixedly connected with said feed path forming member; and
    liquid feed tubes fixedly mounted on said mounting member and extending toward said outer wall of said rinse vessel, said spray heads being disposed on respective ends of said liquid feed tubes.

4. An apparatus according to claim 1, further comprising at least one additional pair of opposing spray heads, at least one opposing pair of said spray heads being connected with a feed path for supplying a sterilizing solution, the remaining spray heads being connected with a second feed path for supplying cleaning water.

5. An apparatus according to claim 1, wherein said means for feeding a liquid comprises a hollow drive shaft rotatably disposed at said center of said rinse vessel, and another hollow liquid feed shaft which is rotatably and loosely fitted in said drive shaft, said drive shaft and said feed shaft defining a gap therebetween, the hollow interior of said feed shaft forming a first feed path, said gap forming a second feed path, one of said feed paths being for supplying cleaning water and the other of said feed paths being for supplying a sterilizing solution.

6. An apparatus according to claim 1, wherein said drive means comprises a hollow drive shaft rotatably disposed at said center of said rinse vessel and having said spray heads integrally mounted thereon, and a motor for driving said drive shaft for rotation.

7. An apparatus according to claim 1, wherein said first and second spray heads are respectively disposed generally above and generally below said cleaning position.

8. An apparatus according to claim 1, wherein said rinse vessel has a top portion and a bottom portion, and wherein said conical support plane slopes toward said bottom portion and said center of said rinse vessel.

* * * * *